United States Patent [19]

Hölderich et al.

[11] Patent Number: 5,105,022
[45] Date of Patent: Apr. 14, 1992

[54] PREPARATION OF 1,2-DIALKOXYETHENES

[75] Inventors: Wolfgang Hölderich, Frankenthal; Dieter Köfer, Ludwigshafen; Werner Bertleff, Viernheim, all of Fed. Rep. of Germany

[73] Assignee: BASF Aktiengesellschaft, Ludwigshafen, Fed. Rep. of Germany

[21] Appl. No.: 581,195

[22] Filed: Sep. 11, 1990

Related U.S. Application Data

[63] Continuation of Ser. No. 228,725, Aug. 5, 1988, abandoned.

[30] Foreign Application Priority Data

Aug. 6, 1987 [DE] Fed. Rep. of Germany ....... 3726126

[51] Int. Cl.$^5$ .............................................. C07C 41/01
[52] U.S. Cl. ................................... 568/673; 568/626; 568/660; 568/669; 568/670
[58] Field of Search ............... 568/673, 669, 670, 626, 568/660

[56] References Cited

U.S. PATENT DOCUMENTS

| | | | |
|---|---|---|---|
| 2,479,068 | 8/1949 | Gresham et al. | 260/615 |
| 3,285,967 | 11/1966 | Schaeffer . | |
| 3,739,032 | 6/1973 | Wunder . | |

FOREIGN PATENT DOCUMENTS

| | | |
|---|---|---|
| 0217089 | 8/1986 | European Pat. Off. . |
| 0254976 | 2/1988 | European Pat. Off. . |
| 2091259 | 7/1982 | United Kingdom . |

OTHER PUBLICATIONS

Zwolinski, Journal of Chemical and Engineering Data, vol. 18, 1973, pp. 441–445.
Patent Abstract of Japan, No. 57-185,232, vol. 7 (1983).

Primary Examiner—Howard T. Mars
Attorney, Agent, or Firm—Keil & Weinkauf

[57] ABSTRACT

Dialkoxyethenes of the formula $$R^1O-\underset{\underset{}{|}}{\overset{\overset{R^2}{|}}{C}}=\underset{\underset{}{|}}{\overset{\overset{R^3}{|}}{C}}-OR^4 \quad (I)$$

where $R^1$ to $R^4$ are identical or different and are each straight-chain or branched alkyl or cycloalkyl or $R^2$ and $R^3$ may furthermore be hydrogen, aryl or alkenylaryl, and the aromatic may be substituted by further radicals, such as alkyl, alkoxy or halogens, are prepared by a process in which an alcohol of the formula $R^4$ OH or $R^5$ OH is eliminated from a trialkoxyethane of the formula (II)

$$R^1O-\underset{\underset{H}{|}}{\overset{\overset{R^2}{|}}{C}}-\underset{\underset{OR^5}{|}}{\overset{\overset{R^3}{|}}{C}}-OR^4 \quad (II)$$

where $R^1$ to $R^4$ have the above meanings and $R^5$ is straight-chain or branched alkyl or cycloalkyl, in the presence of a zeolite and/or a phosphate and/or phosphoric acid or boric acid on a carrier and/or an acidic, untreated metal oxide as a catalyst. Zeolites of the pentasil type are preferably used as catalysts.

7 Claims, No Drawings

PREPARATION OF 1,2-DIALKOXYETHENES

This application is a continuation of application Ser. No. 07/228,725 is filed on Aug. 5, 1988, abandoned.

The present invention relates to a process for the preparation of 1,2-dialkoxyethenes by eliminating an alcohol from a 1,1,2-trialkoxyalkane.

Dialkoxyethenes are used, for example, as monomers or comonomers. The polymerization takes place in the presence of Lewis acids. There are essentially two known methods for the preparation of dialkoxyethenes. H. Baganz et al., in Chem. Ber. 96 (1963), 2657, describe the synthesis of 1,2-dialkoxyethenes from 1,2-dialkoxy-1,2-dichloroethane by elimination of chlorine using magnesium. In this procedure, undesirable magnesium chloride is inevitably obtained.

The second method for the preparation of dialkoxyethenes is the elimination of an alcohol from a 1,1,2-trialkoxyethane. The cleavage of the trialkoxyethane is advantageously carried out in the gas phase over a fixed bed catalyst. For example, U.S. Pat. No. 2,479,068 discloses that 1,1,2-trialkoxyethanes can be cleaved at from 300° to 450° C. over barium hydroxide on silica gel to give 1,2-dialkoxyethenes. H. Baganz et al. describe the use of cerium oxide or magnesium oxide-doped iron oxide on pumice at from 290° to 360° C. [Chem. Ber. 86 (1953), 148–154 and 395–400]. However, this procedure gives a yield of only 27%.

It is also known that alumina pretreated with bases can be used as a catalyst. The reaction temperature for the elimination of methanol from 1,1,2-trimethoxyethane to give 1,2-dimethoxyethene is 300° C. [J. Chem. Eng. Data, 18 (1973), 441]. The yield is 87% and a cis/trans ratio of 8 is obtained.

An alumina catalyst containing sodium hydrogen sulfate gave similar results (G. Bier and N. Vollkommer, Angew. Makromol Chem. 87 (1980), 137). The required reaction temperature for the preparation of 1,2-dimethoxyethene from 1,1,2-trimethoxyethane is given as 350° C.

It is an object of the present invention to prepare 1,2-dialkoxyethenes without secondary reactions at the double bond or at the alkoxy group in a simple manner from readily available starting materials, very high conversion and high selectivity of the catalyst coupled with very long catalyst lives being desirable.

We have found that this object is achieved, and that improved conversions and selectivities coupled with long catalyst lives can be obtained in the preparation of 1,2-dialkoxyethenes of the formula (I)

where $R^1$ to $R^4$ are identical or different and are each straight-chain or branched alkyl or cycloalkyl or $R^2$ and $R^3$ may furthermore be hydrogen, aryl or alkenylaryl, and the aromatic may be substituted by further radicals which are inert under the reaction conditions, such as alkyl, alkoxy or halogen, if an alcohol of the formula $R^5OH$ or $R^4OH$ is eliminated from a 1,1,2-trialkoxyethane of the formula (II)

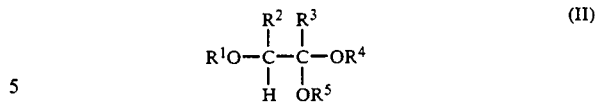

where $R^1$ to $R^4$ have the above meanings and $R^5$ is straight-chain or branched alkyl or cycloalkyl, in the presence of a zeolite and/or a phosphate and/or phosphoric acid or boric acid on a carrier and/or an acidic oxide of the elements Ti, Zr, B, W, Mo, Nb or Cr as a catalyst.

Another advantage of the novel process is that it is also possible to control the isomer distribution of the cis/trans product mixture via the catalyst in an advantageous manner.

Regardless of $R^1$, $R^4$ and $R^5$, suitable radicals $R^2$ and $R^3$ are hydrogen and straight-chain or branched alkyl of 1 to 12, in particular 1 to 8, preferably 1 to 4, carbon atoms, e.g. methyl, ethyl, n-butyl, isobutyl, pentyl, hexyl, octyl or decyl.

Cycloalkyl is, for example, cyclopentyl, cyclohexyl, cycloheptyl, cyclopentenyl or cyclohexenyl.

Examples of aromatic radicals are phenyl, benzyl, toluyl and phenylethyl.

Examples of suitable radicals $OR^1$, $OR^4$ and $OR^5$ are methoxy, ethoxy, n-propoxy, isopropoxy, n-butoxy, isobutoxy, tert-butoxy and hexyloxy.

For example, the following compounds can be used: 1,1,2-trimethoxyethane, 1,1,2-triethoxyethane, 1,1-dimethoxy-2-ethoxyethane, 1,1,2-tripropoxyethane, 1,1,2-tributoxyethane and 1,1-diethoxy-2-propoxyethane.

Advantageously used catalysts for the novel process are acidic zeolite catalysts. Zeolites are crystalline aluminosilicates which have a highly ordered structure with a rigid 3-dimensional network of $SiO_4$ and $AlO_4$ tetrahedra which are bonded by common oxygen atoms. The ratio of Si and Al atoms to oxygen is 1:2 (see Ullmanns Encyclopädie d. techn. Chemie, 4th Edition, Volume 24, page 575 (1983)). The electrovalency of the aluminum-containing tetrahedra is balanced by the inclusion of cations in the crystal, for example an alkali metal ion or hydrogen ion. Cation exchange is possible. The voids between the tetrahedra are occupied by water molecules prior to dehydration by drying or calcination.

In the zeolites, other elements, such as B, Ga, Fe, Cr, V, As, Sb, Bi or Be, or mixtures of these may be incorporated into the framework instead of aluminum, or the silicon may be replaced by a tetravalent element, such as Ge, Ti, Zr or Hf.

Depending on their structure, zeolites are divided into different groups. For example, the zeolite structure is formed by chains of tetrahedra in the mordenite group or by sheets of tetrahedra in the chabasite group, while in the faujasite group the tetrahedra are arranged to form polyhedra, for example in the form of a cubooctahedron, which is composed of 4-membered rings and 6-membered rings. Depending on the bonding of the cubooctahedra, which gives rise to cavities and pores of different sizes, a distinction is made between zeolites of type A, L, X and Y.

Suitable catalysts for the novel process are zeolites of the mordenite group or fine-pore zeolites of the erionite or chabasite type or zeolites of the faujasite type, for example Y, X or L zeolites. This group of zeolites also includes the ultrastable zeolites of the faujasite type, i.e. dealuminated zeolites. Processes for the preparation of such zeolites are described in U.S. Pat. No. 4,512,961.

Zeolites of the pentasil type are particularly advantageous. They have, as a common basic building block, a 5-membered ring composed of $SiO_4$ tetrahedra. They possess a high $SiO_2/Al_2O_3$ ratio and pore sizes which are between those of the zeolites of type A and those of type X or Y.

These zeolites may have different chemical compositions. They are aluminosilicate, borosilicate, iron silicate, beryllium silicate, gallium silicate, chromium silicate, arsenosilicate, antimony silicate and bismuth silicate zeolites or mixtures of these, and aluminogermante, borogermante, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in polyamines, such as 1,6-hexanediamine or 1,3-propanediamine or triethylenetetramine solution, with or, in particular, without the addition of an alkali or alkaline earth, at from 100° to 220° C., under autogenous pressure. These include the isotactic zeolites according to European Patents 34,727 and 46,504. Depending on the choice of the amounts of starting materials, the aluminosilicate zeolites obtained have an $SiO_2/Al_2O_3$ ratio of from 10 to 40,000. Such aluminosilicate zeolites can be synthesized in an ether medium, such as diethylene glycol dimethyl ether, in an alcoholic medium, such as methanol or butane-1,4-diol, or in water.

The borosilicate zeolite is synthesized, for example, at from 90° to 200° C. under autogenous pressure by reacting a boron compound, e.g. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These include the isotactic borosilicate zeolites according to European Patents 34,727 and 46,504. Such borosilicate zeolites can also be prepared if the reaction is carried out in solution in ether, e.g. diethylene glycol dimethyl ether or in alcoholic solution, e.g. hexane-1,6-diol, instead of in aqueous amine solution.

Iron silicate zeolites are obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth, at from 100° to 220° C. under autogeneous pressure.

The silicon-rich zeolites which can be used ($SiO_2/Al_2O_3 \geq 10$) include the ZSM types, ferrierite, Nu-1 and Silicalit ®, a molecular sieve, i.e. a silica polymorph.

The aluminosilicate, borosilicate and iron silicate zeolites prepared in this manner can be isolated, dried at from 100° to 160° C., preferably 110° C., and calcined at from 450° to 550° C., preferably 500° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Suitable catalysts are also obtained if, for example, the aluminosilicate or borosilicate zeolite isolated is molded directly after drying and is not subjected to calcination until after the molding procedure. The aluminosilicate and borosilicate zeolites prepared can be used in pure form, without a binder, as extrudates or pellets, the extrusion or peptizing assistants used being, for example, ethylcellulose, stearic acid, potato starch, formic acid, oxalic acid, acetic acid, nitric acid, ammonia, amines, silicoesters and graphite or mixtures of these.

If, because of its method of preparation, the zeolite is not in the catalytically active, acidic H form but, for example, in the Na form, the latter can be converted completely or partially into the desired H form by ion exchange, for example with ammonium ions, and subsequent calcination, or by treatment with acids.

If, when the zeolite catalysts are used, deactivation due to coking occurs, it is advisable to regenerate the zeolites by burning off the coke deposit with air or with an air/$N_2$ mixture at from 400° to 550° C., preferably 500° C. As a result, the zeolites regain their initial activity.

By precoking, it is possible to adjust the activity of the catalyst to obtain optimum selectivity with respect to the desired reaction product.

In order to obtain very high selectivity, high conversion and long catalyst lives, it is advantageous to modify the zeolites. In a suitable method of modifying the catalysts, the unmolded or molded zeolites are doped with metal salts by ion exchange or by impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4–8, such as Ti, Zr, V, Nb, Cr, Mo, W, Mn, Re, Fe, Ru, Os, Co, Rh, Sr, Ni, Pd or Pt, transition metals of subgroups 1 and 2, such as Cu, Ag or Zn, and rare earth metals, such as La, Ce, Pr, Nd, Fr, Yb or U.

The doping is advantageously carried out as follows: the molded zeolite is initially taken in a riser tube and an aqueous or ammoniacal solution of a halide or of a nitrate of the metals described above is passed over the said zeolite at from 20° to 100° C. Ion exchange of this type can be carried out on the hydrogen, ammonium or alkali metal form of the zeolite. In another possible method of applying metals to the zeolite, the zeolite material is impregnated with, for example, a halide, a nitrate or an oxide of the metals described above, in aqueous, alcoholic or ammoniacal solution. Both ion exchange and impregnation can be followed by one or more drying steps and, if desired, repeated calcination.

In a possible embodiment, for example, $Cu(NO_3)_2 \cdot 3H_2O$ or $Ni(NO_3)_2 \cdot 6H_2O$ or $Ce(NO_3)_3 \cdot 6 H_2O$ or $La(NO_3)_2 \cdot 6H_2O$ or $Cs_2CO_3$ is dissolved in water and this solution is used to impregnate the molded or unmolded zeolite for a certain time, i.e. about 30 minutes. Any supernatant solution is freed from water in a rotary evaporator. Thereafter, the impregnated zeolite is dried at about 150° C. and calcined at about 550° C. This impregnation process can be carried out several times in succession in order to obtain the desired metal content.

It is also possible to prepare an aqueous $Ni(NO_3)_2$ solution or ammoniacal $Pd(NO_3)_2$ solution and to suspend the pure zeolite powder therein at from 40° to 100° C. for about 24 hours, while stirring. After filtration, drying at about 150° C. and calcination at about 550° C., the zeolite material thus obtained can be further processed with or without a binder to give extrudates, pellets or fluidizable material.

The zeolite in the H form or ammonium form or alkali metal form can be subjected to ion exchange by a method in which the zeolite, in the form of extrudates or pellets, is initially taken in a column and, for example, an aqueous $Ni(NO_3)_2$ solution or ammoniacal $Pd(NO_3)_2$ solution is circulated over the said zeolite at slightly elevated temperatures of from 30° to 80° C. for from 15 to 20 hours. The product is then washed with water, dried at about 150° C. and calcined at about 550° C. In the case of some metal-doped zeolites, for example Pd-, Cu- or Ni-doped zeolites, an aftertreatment with hydrogen is advantageous.

In another possible method of modification, the molded or unmolded zeolite material is subjected to a treatment with acids, such as hydrochloric acid, hydrofluoric acid and phosphoric acid and/or steam. This procedure is advantageously carried out as follows: zeolites in powder form are treated with 1N phosphoric acid for 1 hour at 80° C. After the treatment, the product is washed with water, dried at 110° C. for 16 hours and calcined at 500° C. for 20 hours. In another procedure, zeolites, before or after they have been molded with binders, are treated with a 3-25, in particular 12-20% strength by weight aqueous hydrochloric acid, for example for from 1 to 3 hours at from 60° to 80° C. The zeolite treated in this manner is then washed with water, dried, and calcined at from 400° to 500° C.

In a particular embodiment of the acid treatment, the zeolite material, before it has been molded, is treated at elevated temperatures with 0.001-2N, preferably 0.05-0.5N, hydrofluoric acid, for example by refluxing for from 0.5 to 5, preferably from 1 to 3, hours. After the zeolite material has been isolated by filtering it off and washing it thoroughly, it is advantageously dried at from 100° to 160° C. and calcined at from 450° to 600° C. In another preferred embodiment of the acid treatment, the zeolite material is molded with a binder and then treated at elevated temperatures, advantageously at from 50° to 90° C., preferably from 60° to 80° C., for from 0.5 to 5 hours with 12-20% strength by weight hydrochloric acid. The zeolite material is then washed thoroughly and advantageously dried at from 100° to 160° C. and calcined at from 450° to 600° C. An HF treatment can also be followed by an HCl treatment.

Further catalysts for the novel process are phosphates, in particular aluminum phosphates, silicon aluminum phosphates, silicon iron aluminum phosphates, cerium phosphate, zirconium phosphates, boron phosphate, iron phosphate or mixtures of these.

In particular, aluminum phosphates synthesized under hydrothermal conditions are used as aluminum phosphate catalysts for the novel process.

The aluminum phosphates prepared under hydrothermal conditions are, for example, APO-5, APO-9, APO11, APO-12, APO-14, APO-21, APO-25, APO-31 and APO-33. Syntheses of these compounds are described in European Patent 132,708 and U.S. Pat. Nos. 4,310,440 and 4,473,663.

For example, $AlPO_4$-5 (APO-5) is synthesized by mixing orthophosphoric acid with pseudoboehmite (Catapal SB ®) in water to give a homogeneous mixture; tetrapropylammonium hydroxide is added to this mixture, and the reaction is then carried out at about 150° C. for from 20 to 60 hours under autogenous pressure in an autoclave. The $AlPO_4$ filtered off is dried at from 100° to 160° C. and calcined at from 450° to 550° C.

$AlPO_4$-9 (APO-9) is likewise synthesized from orthophosphoric acid and pseudoboehmite, but in aqueous DABCO solution (1,4-diazabicyclo[2.2.2]octane) at about 200° C. under autogenous pressure in the course of from 200 to 400 hours.

$AlPO_4$-21 (APO-21) is synthesized from orthophosphoric acid and pseudoboehmite in aqueous pyrrolidone solution at from 150° to 200° C. under autogenous pressure in the course of from 50 to 200 hours.

The silicon aluminum phosphates used for the novel process are, for example, SAPO-5, SAPO-11, SAPO-31 and SAPO-34. The synthesis of this compound is described in, for example, European Patent 103,117 and U.S. Pat. No. 4,440,871. SAPOs are prepared by crystallization from an aqueous mixture at from 100° to 250° C. and under autogenous pressure in the course of from 2 hours to 2 weeks, the reaction mixture of a silicon, aluminum and phosphorus component in aqueous solutions containing organic amines being reacted.

For example, SAPO-5 is obtained by mixing $SiO_2$, suspended in aqueous tetrapropylammonium hydroxide solution, with an aqueous suspension of pseudoboehmite and orthophosphoric acid and then carrying out the reaction at from 150° to 200° C. in the course of from 20 to 200 hours under autogenous pressure in a stirred autoclave. The powder is filtered off, dried at from 110° to 160° C. and calcined at from 450° to 550° C.

Precipitated aluminum phosphates can also be used as phosphate catalysts in the process. For example, an aluminum phosphate of this type is prepared by dissolving 92 g of diammonium hydrogen phosphate in 700 ml of water. 260 g of $Al(NO_3)_3 \cdot H_2O$ in 700 ml of water are added dropwise to this solution in the course of 2 hours. During this procedure, the pH is kept at 8 by the simultaneous addition of 25% strength $NH_3$ solution. The precipitate formed is stirred for a further 12 hours, after which it is filtered off under suction and washed thoroughly. It is dried at 60° C. for 16 hours.

Boron phosphates for the novel process can be prepared, for example, by mixing and kneading concentrated boric acid and phosphoric acid and by subsequent drying and calcination in an inert gas, air or steam atmosphere at from 250° to 650° C., preferably from 300° to 500° C..

Modifying components, as described above in the case of the zeolites, can be applied to these phosphates by impregnation (immersion and spraying) or, in some cases, also by ion exchange. The zeolite catalysts can also be modified by acids.

Other suitable acidic, untreated catalysts are, for example, the acidic oxides of the elements Ti, Zr, Si, Al, V, W, Mo, Nb and Cr. These are titanium dioxide, zirconium dioxide, vanadium oxides, niobium oxides, chromium oxides, molybdenum oxides, tungsten oxides or mixtures of these oxides. Thus, 1,2-dimethoxyethene can be prepared in good yields by eliminating methanol from 1,1,2-trimethoxyethane by the novel process using these catalysts.

It is also possible to use catalysts impregnated with phosphoric acid or boric acid. Phosphoric acid or boric acid is, for example, applied to $SiO_2$, $Al_2O_3$ or pumice carriers, for example by impregnation or spraying. A catalyst containing phosphoric acid can be obtained, for example, by impregnating $SiO_2$ with $H_3PO_4$ and then carrying out drying and calcination. However, phosphoric acid can also be sprayed together with silica gel in a spray tower; this is followed by drying and, generally, calcination. Phosphoric acid can also be sprayed onto the carrier in an impregnating mill.

The catalysts described here can be used alternatively in the form of 2-4 mm extrudates, pellets of 3-5 mm diameter or chips having particle sizes of from 0.1 to 0.5 mm, or as a fluidized catalyst.

The conversion according to the invention is, as a rule, preferably carried out in the gas phase at from 100° to 450° C., in particular from 150° to 350° C., preferably from 250° to 300° C., and at a WHSV of from 0.1 to 20, preferably from 0.5 to 5, h$^{-1}$ (g of starting mixture per g of catalyst per hour), in a fixed bed or fluidized bed.

It is also possible to carry out the reaction in the liquid phase (suspension, trickle-bed or liquid phase method) at from 50° to 200° C.

The process is, as a rule, carried out under atmospheric pressure or, depending on the volatility of the starting compound, under reduced or superatmospheric pressure; it is preferably carried out continuously or may also be effected batchwise.

Sparingly volatile or solid starting materials are used in dissolved form, for example in solution in tetrahydrofuran, toluene or petroleum ether. In general, it is possible to dilute the educt with such solvents or with inert gases, such as $N_2$, Ar or steam.

After the reaction, the resulting products are isolated from the reaction mixture by a conventional method, for example by distillation; unconverted starting materials are, if desired, recycled to the reaction.

The gaseous reaction products are preferably separated immediately into their individual components, for example in a fractionation column, to prevent a back-reaction and to obtain a high conversion. As complete conversion as possible facilitates working up of the product mixture, particularly with regard to the separation of trimethoxyethene and dimethoxyethylene.

EXAMPLES 1-23

The reactions in the gas phase are carried out under isothermal conditions in a tube reactor (coil, 0.6 cm internal diameter, 9 cm length) in the course of not less than 6 hours. The reaction products are isolated by conventional methods and characterized. Quantitative determination of the reaction products and of the starting materials is carried out by gas chromatography.

The catalysts used for the novel process are:

Catalyst A

The borosilicate zeolite of the pentasil type is prepared in a hydrothermal synthesis from 640 g of finely divided $SiO_2$, 122 g of $H_3BO_3$ and 8000 g of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and calcined at 500° C. for 24 hours. This borosilicate zeolite is composed of 94.2% by weight of $SiO_2$ and 2.3% by weight of $B_2O_3$.

This material is molded with a molding assistant to give 2 mm extrudates, which are dried at 110° C. for 16 hours and calcined at 500° C. for 24 hours.

Catalyst B

An aluminosilicate zeolite of the pentasil type is prepared under hydrothermal conditions, under autogenous pressure and at 150° C., from 65 g of finely divided $SiO_2$ and 20.3 g of $Al_2(SO_4)_3 \cdot 18H_2O$ in 1 kg of an aqueous 1,6-hexanediamine solution (weight ratio 50:50) in a stirred autoclave. The crystalline reaction product is filtered off, washed thoroughly, dried at 110° C. for 24 hours and then calcined at 500° C. for 24 hours. This aluminosilicate zeolite contains 91.6% by weight of $SiO_2$ and 4.6% by weight of $Al_2O_3$. The catalyst is molded with a molding assistant to give 2 mm extrudates, which are dried at 110° C. for 16 hours and calcined at 500° C. for 24 hours.

Catalyst C

Catalyst C is obtained by impregnating the extrudates of catalyst A with an aqueous $Cs_2CO_3$ solution and then drying the product at 130° C. for 2 hours and calcining it at 540° C. for 2 hours. The Cs content is 0.6% by weight.

Catalyst D 200 g of the borosilicate zeolite described in the case of catalyst A are subjected to ion exchange with 1 l of an aqueous solution of 16.7 g of $FeCl_3 \cdot 6H_2O$ and 50 g of $NH_4Cl$ for 24 hours at room temperature, then washed thoroughly with $H_2O$ until Cl-free, dried at 150° C. for 1 hour and calcined at 500° C. for 2 hours. This powder is molded with finely divided $SiO_2$ in a weight ratio of 70:30. After drying, the extrudates are calcined at 500° C. for 16 hours.

Catalyst E

Catalyst E is obtained by impregnating the extrudates of catalyst A with an aqueous solution of cerium nitrate and palladium nitrate and then drying the product at 130° C. for 2 hours and calcining it at 540° C. for 2 hours. The Ce content is 2.3% by weight and the Pd content is 0.5% by weight.

Catalyst F

Catalyst F is prepared in the same manner as catalyst C, except that $Cs_2CO_3$ is replaced by $Fe(NO_3)_3$. The Fe content is 2.9% by weight.

Catalyst G

The iron silicate zeolite of the pentasil type is synthesized under hydrothermal conditions, under autogenous pressure and at 165° C., from 273 g of waterglass, dissolved in 253 g of an aqueous 1,6-hexandiamine solution (weight ratio 50:50), and 31 g of iron sulfate, dissolved in 21 g of 96% strength sulfuric acid and 425 g of water, in a stirred autoclave in the course of 4 days. The zeolite is filtered off, washed thoroughly, dried at 110° C. for 24 hours and calcined at 500° C. for 24 hours. An iron silicate zeolite having an $SiO_2/Fe_2O_3$ ratio of 17.7 and an $Na_2O$ content of 1.2% by weight is obtained. The catalyst is extruded with finely divided $SiO_2$ in a weight ratio of 70:30 to give 2.5 mm extrudates, which are dried at 110° C. for 16 hours and calcined at 500° C. for 24 hours. These extrudates are subjected to ion exchange with a 20% strength $NH_4Cl$ solution at 80° C. and then washed chloride-free, dried at 110° C. and calcined at 500° C. for 5 hours. Ion exchange is continued until the Na content is 0.002% by weight.

Catalyst H

Catalyst H is prepared in the same manner as catalyst C, except that $Cs_2CO_3$ is replaced by $Ce(NO_3)_2$. The Ce content is 1.8% by weight.

Catalyst I

This is prepared in the same way as catalyst H, except that the Ce content is 1.2% by weight.

Catalyst J

Catalyst J is prepared in the same manner as catalyst C, except that $Cs_2CO_3$ is replaced by $Cr(NO_3)_3$. The Cr content is 1.9% by weight.

Catalyst K $AlPO_4$-12 (APO-12) is synthesized by dissolving 200 g of 98% strength phosphoric acid and suspending 136 g of boehmite in 400 g of water, adding an aqueous solution of 60 g of ethylenediamine and 320 g of $H_2O$ and reacting this mixture in a stirred autoclave at 200° C. in the course of 24 hours under autogenous pressure. The crystalline material is filtered off, dried at 120° C. and then calcined at 500° C. for 16 hours. The $AlPO_4$-12 synthesized in this manner contains 55.5% by weight of $P_2O_5$ and 39.7% by weight of $Al_2O_3$. This material is molded with molding assistants to give 3 mm extrudates, which are dried repeatedly at 120° C. and calcined for 6 hours at 500° C.

Catalyst L $AlPO_4$-5 (APO-5) is synthesized by stirring together 200 g of 95% strength phosphoric acid, dissolved in 325 g of $H_2O$, 136 g of boehmite and 678 g of 30% strength tetrapropylammonium hydroxide and then carrying out the reaction at 150° C. under autogenous pressure in the course of 43 hours. The product which has been dried at 120° C. and calcined for 16 hours at 500° C. contains 46.5% by weight of $P_2O_5$ and 45.5% by weight of $Al_2O_3$. This $AlPO_4$-5 is molded with boehmite in a weight ratio of 60:40 to give 2 mm extrudates, which are dried at 110° C. and calcined for 16 hours at 500° C.

Catalyst M

Silicon aluminum phosphate-5 (SAPO-5) is prepared from a mixture of 200 g of 98% strength phosphoric acid, 136 g of boehmite, 60 g of 30% strength silica sol, 287 g of tripropylamine and 587 g of $H_2O$. This mixture is reacted at 150° C. under autogenous pressure in the course of 168 hours. The crystalline product is filtered off, dried at 120° C. and calcined at 500° C. SAPO-5 contains 49.8% by weight of $P_2O_5$, 33.0% by weight of $Al_2O_3$ trusion assistant to give 3 mm extrudates, which are dried at 120° C. and calcined at 500° C.

Catalyst N

Commercial zirconium phosphate $Zr_3(PO_4)_4$ is molded in pure form.

Catalyst O $BPO_4$ is prepared by combining 49 g of $H_3BO_3$ with 117 g of 75% strength $H_3PO_4$ in a kneader, evaporating off excess water and molding the reaction product to give 3 mm extrudates. These extrudates are dried at 110° C. and calcined at 350° C. Catalyst O contains 8.77% by weight of B and 28.3% by weight of P.

Catalyst P

Catalyst P is a precipitated aluminum phosphate which is obtained by precipitation from $Al(NO_3)_3$/$H_3PO_4$ solution with $NH_3$ at pH 6-7. The precipitate is filtered off, dried at 110° C. and then calcined at 500° C. Catalyst P contains 28.5% by weight of Al and 13.2% by weight of P.

Catalyst Q

Commercial NaY zeolite is extruded with a molding assistant to give 2 mm extrudates, which are dried at 110° C. and calcined for 16 hours at 500° C. and subjected to ion exchange with 20% strength ammonium chloride solution. The residual sodium content of catalyst Q is 0.85% by weight (calcined at 500° C.).

Catalyst R

Catalyst R is commercial mordenite (Zeolon 900 H®) in the H form.

Catalyst S $TiO_2$ P 25® is molded to give 2 mm extrudates, which are dried at 110° C. and calcined for 16 hours at 500° C.

Catalyst T

Commercial $SiO_2$ (D 11-10®).

Catalyst U $Al_2O_3$ (D 10-10®) is impregnated with $H_3BO_3$, dried at 110° C. and calcined for 5 hours at 500° C. Catalyst U is composed of 85% of $Al_2O_3$ and 15% of $B_2O_3$.

The experimental results obtained with these catalysts and the experimental conditions are summarized in Table 1.

Table 1 shows that the cis/trans ratio can be influenced by the choice of the catalyst; the phosphate catalysts generally give a higher proportion of the trans compound. The selectivity in the case of the phosphates having a zeolite structure is higher than that for the phosphates which do not have a zeolite structure.

TABLE 1

| | Trimethoxyethane(II) → dimethoxyethylene(I) + methanol | | | | | | | | | | |
|---|---|---|---|---|---|---|---|---|---|---|---|
| Example | 1[1] | 2[1] | 3[2] | 4[1] | 5[2] | 6[1] | 7[1] | 8[1] | 9[1] | 10[1] | 11[1] |
| Catalyst | A | A | A | B | C | D | E | F | G | H | I |
| Temperature | 250 | 300 | 250 | 300 | 300 | 300 | 300 | 300 | 300 | 300 | 300 |
| WHSV $h^{-1}$ | 3.5 | 3.5 | 2.5 | 2 | 1 | 2 | 1.5 | 2 | 3 | 2 | 3 |
| Conversion (II) % | 92.8 | 98.0 | 96.9 | 98.4 | 97.6 | 91.0 | 92.1 | 99.0 | 98.4 | 97.4 | 99.5 |
| Selectivity (I) % trans | 32.6 | 33.1 | 32.8 | 28.8 | 33.4 | 32.1 | 23.7 | 32.2 | 31.4 | 33.3 | 31.4 |
| Selectivity (I) % cis | 56.6 | 51.2 | 55.3 | 58.7 | 51.5 | 52.1 | 44.9 | 50.5 | 49.8 | 53.4 | 57.9 |
| Selectivity Σ | 89.2 | 84.3 | 88.1 | 87.5 | 84.9 | 84.2 | 68.6 | 82.7 | 81.3 | 86.7 | 89.3 |
| Example | 12[1] | 13[1] | 14[1] | 15[1] | 16[1] | 17[1] | 18[1] | 19[1] | 20[1] | 21[1] | 22[1] | 23[1] |

TABLE 1-continued

| Trimethoxyethane(II) → dimethoxyethylene(I) + methanol | | | | | | | | | | | | |
|---|---|---|---|---|---|---|---|---|---|---|---|---|
| Catalyst | J | Q | R | K | L | M | N | O | P | S | T | U |
| Temperature | 300 | 300 | 300 | 300 | 300 | 300 | 300 | 300 | 300 | 300 | 300 | 300 |
| WHSV $h^{-1}$ | 1 | 1 | 2 | 3 | 2 | 2 | 2 | 2.5 | 1.5 | 1.5 | 3.5 | 2.5 |
| Conversion (II) % | 98.6 | 89.6 | 55.5 | 91.6 | 98.6 | 65.3 | 81.2 | 85.5 | 98.5 | 84.9 | 98.9 | 99 |
| Selectivity (I) % trans | 28.9 | 23.9 | 29.1 | 23.4 | 29.7 | 25.7 | 22.6 | 19.1 | 32.5 | 15.3 | 27.1 | 27.3 |
| Selectivity (I) % cis | 52.7 | 63.5 | 65.2 | 72.9 | 65.4 | 67.7 | 67.3 | 67.0 | 52.3 | 65.2 | 52.7 | 49.1 |
| Selectivity Σ | 81.6 | 87.4 | 94.3 | 96.3 | 95.1 | 93.4 | 89.9 | 86.1 | 84.8 | 80.5 | 79.8 | 76.4 |

[1] 50:50 (w/w) tetrahydrofuran solution
[2] Used in pure form

We claim:

1. A process for the preparation of a dialkoxyethene of the formula (I)

$$R^1O-\underset{\underset{}{|}}{C}=\underset{\underset{}{|}}{C}-OR^4 \quad\quad (I)$$
$$\phantom{R^1O-}R^2\phantom{=}R^3$$

where $R^1$ to $R^4$ are identical or different and are each straight-chain or branched alkyl or cycloalkyl and $R^2$ and $R^3$ may independently be hydrogen, aryl or alkenylaryl, and the aromatic ring may be substituted by radicals selected from the group consisting of alkyl, alkoxy and halogen, which process comprises contacting a trialkoxyethane of the formula (II)

$$R^1O-\underset{\underset{H}{|}}{\overset{\overset{R^2}{|}}{C}}-\underset{\underset{OR^5}{|}}{\overset{\overset{R^3}{|}}{C}}-OR^4 \quad\quad (II)$$

where $R^1$ to $R^4$ have the above meanings and $R^5$ is a straight-chain or branched alkyl or cycloalkyl with a catalytic amount of a catalyst selected form the group consisting of (1) acidic zeolite, (2) a phosphate of Zr, (3) a phosphate of Fe, (4) an aluminum phosphate synthesized under hydrothermal conditions, and (5) mixtures of these in the gaseous phase.

2. A process for the preparation of 1,2-dimethoxyethene, which process comprises contacting 1,1,2-trimethoxyethane with a catalytic amount of a catalyst selected form the group consisting of (1) acidic zeolite, (2) a phosphate of Zr, (3) a phosphate of Fe, (4) an aluminum phosphate synthesized under hydrothermal conditions, and (5) a mixture of these in the gaseous phase.

3. A process as defined in claim 1 wherein the catalyst is an aluminosilicate zeolite of the Y type.

4. A process as defined in claim 1 wherein the catalyst is an acidic zeolite doped with an alkali metal, a transition metal or a rate earth metal.

5. A process as defined in claim 1 wherein the catalyst is an aluminum phosphate synthesized under hydrothermal conditions.

6. A process as defined in claim 1 wherein the catalyst is a phosphate or Zr, a phosphate of Fe, or a mixture of these.

7. A process as defined in claim 1 wherein the catalyst is a phosphate of Zr.

* * * * *